(12) United States Patent
Adachi et al.

(10) Patent No.: US 6,245,897 B1
(45) Date of Patent: Jun. 12, 2001

(54) MONOCLONAL ANTIBODY RECOGNIZING CELL SURFACE ANTIGEN CD14

(75) Inventors: Yoshiyuki Adachi; Naohito Ohno, both of Hachioji; Toshiro Yadomae, Tama, all of (JP)

(73) Assignee: Seikagaku Kogyo Kabushiki Kaisha (Seikagaku Corporation), Tokyo (JP)

( * ) Notice: Subject to any disclaimer, the term of this patent is extended or adjusted under 35 U.S.C. 154(b) by 0 days.

(21) Appl. No.: 09/262,313

(22) Filed: Mar. 4, 1999

(30) Foreign Application Priority Data

Sep. 7, 1998 (JP) .................................................. 10-253002

(51) Int. Cl.⁷ .............................. C12P 21/08; C12P 21/04; C12N 15/06; C12N 15/10
(52) U.S. Cl. ..................................... 530/388.7; 530/387.1; 530/388.2; 435/70.21; 435/452; 435/362; 435/332; 435/334; 435/345
(58) Field of Search ..................................... 435/452, 440, 435/343, 70.21, 326, 332, 334, 345; 530/387.1, 388.1, 388.7, 388.2, 388.22

(56) References Cited

U.S. PATENT DOCUMENTS 4,701,408 * 10/1987 Koestler .

OTHER PUBLICATIONS

Haslberger et al Journal of Endotoxin Research 4: 431–441, 1997.*
ATTC Cell Lines and Mybridomas Eigth Edition p. 330 Editor May et al, 1994.*

* cited by examiner

Primary Examiner—David Saunders
Assistant Examiner—Amy DeCloux
(74) Attorney, Agent, or Firm—Oblon, Spivak, McClelland, Maier & Neustadt, P.C.

(57) ABSTRACT

A monoclonal antibody which recognizes lipopolysaccharide binding site of macrophage cell surface receptor CD14 and has binding activity to monocyte or macrophage cells. The monoclonal antibody suppresses the production of an inflammatory mediator such as TNF, IL-6 or NO at early stages by recognizing CD14, and competitively inhibiting its binding with LPS. Therefore, it is useful for pathology analysis and the treatment of sepsis.

1 Claim, 5 Drawing Sheets

MONOCLONAL ANTIBODY RECOGNIZING CELL SURFACE ANTIGEN CD14

BACKGROUND OF THE INVENTION

Field of the Invention

The present invention relates to a monoclonal antibody which recognizes the lipopolysaccharide binding site of macrophage cell surface receptor CD14 and has binding activity to monocyte or macrophage cells, and to a process for producing the same.

It also relates to a method for suppressing the production of an inflammatory mediator in a mammal cell which comprises competitively inhibiting binding of the cell surface receptor CD14 with lipopolysaccharide.

When CD14, which is a cell surface receptor having high affinity for lipopolysaccharide (referred to as "LPS" hereinafter), recognizes a complex of LPS and LPS binding protein (referred to as "LBP" hereinafter) in serum (the complex of LPS and LBP is referred to as "LPS-LBP complex" hereinafter), it causes monocytes or macrophages to excrete various factors such as inflammatory cytokines including TNF and IL-6, and NO to the outside of the cells. It has been reported that these factors play extremely important roles in crisis and worsening of sepsis.

The soluble CD14 antigen may also relate closely to the pathology of sepsis, and various pathological analyses of sepsis utilizing antibodies to CD14 antigen have been attempted. For example, International Patent Application Un-examined Publication in Japanese (KOHYO TOKKYO KOHO) No. Hei 8-510909/1996 discloses an antibody produced by a hybridoma which was obtained by imunizing a mouse or a rabbit with a recombinant CD14 as an antigen. Further, International Patent Application Un-examined Publication in Japanese (KOHYO TOKKYO KOHO) No. Hei 5-501399/1993 discloses use of an anti-CD14 monoclonal antibody for the treatment of sepsis, which competitively inhibits the binding of LPS-LBP complex to CD14.

However, these known antibodies were produced by using a recombinant CD14 as an antigen, and therefore they have problems concerning their specificity. For example, they may not show affinity for actual antigens that are present on cellular surfaces in various forms, antibodies having desired recognition characteristics may not be obtained because the recombinant CD14 used as the antigen may denature during its purification, or other problems may arise. Therefore, they have been insufficient for the application to pathology analysis and treatment of sepsis.

Accordingly, the object of the present invention is to provide a monoclonal antibody recognizing the LPS binding site of the macrophage cell surface receptor, CD14, which is useful for pathology analysis and treatment of sepsis and the like.

SUMMARY OF THE INVENTION

The present inventors prepared hybridomas using cells of animals immunized with monocyte or macrophage cells as antigen, screened only hybridoma clones producing antibodies having binding activity to monocyte or macrophage cells by means of a fluorescence-activated cell sorter (FACS), precisely examined molecular characteristics of antigens reacting with those antibodies, and cloned only antibodies binding with the cell surface CD14 antigen. As a result, they found a novel monoclonal antibody which recognizes the LPS binding site of CD14, and suppresses the production of an inflammation mediator such as TNF, IL-6 or NO by competitively inhibiting the binding of CD14 to LPS. Thus, the present invention has been accomplished.

That is, the present invention provides a monoclonal antibody which recognizes the lipopolysaccharide binding site of macrophage cell surface receptor CD14 and has binding activity to monocyte or macrophage cells.

The monoclonal antibody of the present invention is produced by a hybridoma obtained by fusion of an antibody producing cell of a mammal immunized with monocyte or macrophage cells and a myeloma cell. The hybridoma is the 4C1 hybridoma cell line deposited at the National Institute of Bioscience and Human-Technology, Agency of Industrial Science and Technology, 1-3, Higashi 1 chome Tsukuba-Shi Ibarkai-ken 305-8566 JAPAN under the Budapest Treaty under the Accession No. FERM BP-6924. The hybridoma obtained by fusion of an antibody producing cell and a myeloma cell is proliferated in a culture medium or in a living body, and the hybridoma having an ability to produce continuously said antibody is separated.

Accordingly, the present invention also provides a process for producing the monoclonal antibody of the present invention, which comprises proliferating a hybridoma obtained by fusion of an antibody producing cell and a myeloma cell in a culture medium or in a living body, wherein the antibody producing cell is collected from an animal immunized with monocyte or macrophage cells, and wherein the hybridoma having an ability to produce continuously said antibody is separated.

In the aforementioned monoclonal antibody and the process for producing the same of the present invention, the monocyte or macrophage cells are preferably RAW 264.7 cells derived from mouse (ATCC No. TIB71).

The present invention further provides a method for suppressing the production of an inflammatory mediator in a mammal cell, which comprises competitively inhibiting binding of the cell surface receptor CD14 with lipopolysaccharide by utilizing the aforementioned monoclonal antibody of the present invention.

In the aforementioned method for suppressing the production of the inflammatory mediator of the present invention, the inflammatory mediator is preferably TNF-α, IL-6 or NO.

DETAILED DESCRIPTION OF THE INVENTION

The monoclonal antibody of the present invention is a monoclonal antibody which recognizes the LPS binding site of the macrophage cell surface receptor CD14, and has binding activity to monocyte or macrophage cells, and which is produced by a hybridoma obtained by fusion of an antibody producing cell of a mammal immunized with monocyte or macrophage cells, and a myeloma cell.

The production method of the monoclonal antibody of the present invention will be explained in detail hereinafter.

The method per se for the production of the monoclonal antibody of the present invention can be a known one, and the monoclonal antibody can be produced by, for example, the method of Kohler and Milstein (Nature, 256, 495–497 (1975)).

For example, monocyte or macrophage cells derived from mouse or the like are used as the antigen, and they are administered to abdominal cavity, subcutis, footpad or the like of an animal to be immunized such as mouse, rat, guinea pig, rabbit, goat, sheep, horse, pig, dog, cat, chicken or the like. Among these animals, rat is preferably used.

As the macrophage cells, RAW 264.7 cells are preferably used. These cells have an accession No. of ATCC No. TIB71. They are listed in the ATCC Catalogue of CELL LINES & HYBRIDOMAS, 1992, 7th Ed., and can be readily obtained from American Type Culture Collection, Rockville, Md.

The monocyte or macrophage cells are preferably stimulated with LPS or β-D-glucan beforehand.

Antibody producing cells such as spleen cells, lymphocytes, or peripheral blood cells are collected from the immunized animal, and they are fused with myeloma cells, a tumor cell strain, to form hybridoma by the method per se known. A spleen cell is preferable as an antibody producing cell. As the myeloma cells used for the cell fusion, those of cell lines allogenic to the immunized animal are preferably used, whilst cell lines of various mammals can be utilized.

Myeloma cells having a selectable marker such as absence of salvage pathway are preferably used so that unfused cells and fused cells can be distinguished after the cell fusion, and only hybridomas can be proliferated while excluding the unfused myeloma cells. Further, to make the desired antibodies easier to obtain from culture supernatant of hybridomas, it is preferable to use myeloma cells of a strain not excreting endogenous immunoglobulin.

While various known cells can be used as such myeloma cells, and they are not particularly limited, NS-1 cells are preferred. These myeloma cells have an accession No. of ATCC No. TIB18. They are listed in the ATCC Catalogue of CELL LINES & HYBRIDOMAS, 1992, 7th Ed., and can be readily obtained from American Type Culture Collection, Rockville, Md.

The resulting hybridomas are selectively proliferated in a cell culture medium suitable for the selection by the aforementioned marker, for example, in the HAT culture medium containing hypoxanthin (H), aminopterin (A), and thymidine (T), and the supernatant of the culture is screened by using monocyte or macrophage cells in a fluorescence-activated cell sorter to select hybridoma strains continuously producing antibodies specifically binding to the monocyte or macrophage cells.

By culturing the hybridoma strains selected as described above in an appropriate culture medium, monoclonal antibodies can be produced in the culture medium.

Further, a large amount of the monoclonal antibodies can be prepared by culturing the hybridoma strains in living bodies such as in mouse abdominal cavity and isolating the antibodies from ascites or the like.

The monoclonal antibodies obtained as described above may be purified by a conventional method for purification of antibodies. Examples of such antibody purification methods include, for instance, salting-out with sodium sulfate, ammonium sulfate or the like, selective precipitation separation methods by low temperature alcohol precipitation, precipitation with polyethylene glycol, isoelectric precipitation and the like, electrophoresis, ion exchange chromatography utilizing ion exchanger such as diethylamino ester (DEAE) derivatives and carboxymethyl (CM) derivatives of agarose gel, dextran gel or the like, affinity chromatography utilizing protein A or protein G, hydroxyapatite chromatography, imunoadsorption chromatography utilizing immobilized antigens, gel filtration, ultracentrifugation and the like.

While the immunoglobulin class of the monoclonal antibody of the present invention obtained as described above is not particularly limited, that of IgG2b may be exemplified.

Though the monoclonal antibody of the present invention is typically an antibody produced by a hybridoma, antibody fragments obtained by treating such an antibody with a protease not degrading the antigen-binding site (Fab) such as plasmin, pepsin and papain, i.e., Fab, Fab', (Fab')$_2$ and the like, are encompassed by the monoclonal antibody of the present invention, so long as they have the properties of the monoclonal antibody of the present invention.

EXAMPLES

The present invention will be explained hereinafter more specifically with reference to the following examples. However, the examples are given merely for illustration, and the present invention is not limited to them.

Example 1

Production of monoclonal antibodies (a) Immunization $5\times10^7$ of RAW 264.7 cells, which had been preliminarily stimulated with 250 μg/ml of grifolan (β-D-glucan; Adachi et al., Biological Pharm. Bull. 17(12) 1554–1560, 1994) overnight, were intraperitoneally injected to 6-week old male DA rats (Japan SLC) three times at intervals of two weeks.

(b) Preparation of spleen cells

Three days after the third injection, the rats were killed by chloroform anesthesia, and spleens were extracted. They were minced in Dulbecco's modified Eagle medium (DMEM, Nissui Pharmaceutical), and cooled with ice for 5 minutes, and the supernatant was centrifuged at 1200 rpm for 5 minutes. The resulting cells were treated with 15 ml of ACK-solubilization buffer (8.29 g/l NH$_4$Cl, 1 g/l KHCO$_3$, 37.2 mg/l EDTA·2Na, pH 7.2), and washed twice with DMEM to afford $5\times10^8$ cells.

(c) Preparation of myeloma cells

In parallel with the above procedure, mouse myeloma cells NS-1 that had been cultured in RPMI1640 (Nissui Pharmaceutical) culture broth containing 10% fetal calf serum (FCS) were collected, and washed twice with DMEM to prepare $1–3\times10^7$ cells.

(d) Cell fusion

The spleen cells prepared in the above (b) and the NS-1 cells prepared in the above (c) were mixed, centrifuged at 1000 rpm for 5 minutes, and put the centrifugal tube into a 37° C. water bath prepared beforehand, after complete removal of the supernatant. In this water bath at 37° C., the cells were added with 1 ml of 50% polyethylene glycol dissolved in 1 ml of DMEM over 1 minute, subsequently with 2 ml of DMEM over 2 minutes, and slowly with 6 ml of DMEM with stirring. This mixture was centrifuged at 1000 rpm for 5 minutes, and the cells were suspended in 20 ml of 20% FCS-DMEM. Ten milliliters of this suspension was taken with a glass pipet, and inoculated to a 96-well plate in an amount of two drops per well.

(e) Screening and cloning of hybridoma

The plate prepared in the above (d), which had been inoculated with the cells, was incubated in an incubator at 37° C. under 5% $CO_2$ overnight, and then added with HAT selection medium, and the HAT medium was changed every two days for 2 weeks. After 2 weeks, the supernatants of the proliferated cells were screened for hybridoma clones producing antibodies binding to the RAW 264.7 cells by a fluorescence-activated cell sorter (FACS). The positive clones were further cultured and proliferated, and then transferred to a 48-well plate and further cultured. Those positive clones were subjected to limiting dilution. The fused cells were suspended in a growth medium (20% ATCC CCL-46 (medium name) culture supernatant, 20% FCS-DMEM), and inoculated to a 96-well plate so that 1 cell was present in each well. This plate was incubated in an incubator at 37° C. under 5% $CO_2$ for about 2 weeks, and the supernatants of the formed colonies were screened again. The resulting positive clones were subjected to limiting dilution again (0.3 cell/well), and were incubated in an incubator at 37° C. under 5% $CO_2$ for about 2 weeks. The resulting clones were used as hybridomas.

(f) Cultivation of hybridoma

The resulting hybridomas were conditioned by incubating them in DMEM culture broth containing 10% inactivated FCS at 37° C. in the presence of 5% $CO_2$ for several days, and then incubating them in DMEM culture broth containing 5% inactivated FCS. The hybridomas were further conditioned in DMEM culture broth containing about 2% inactivated FCS, and cultivated in culture broth of a serum-free medium, PM-1000 (Eiken Chemical), in an incubator at 37° C. under 5% $CO^2$. For the preparation of antibodies, at least 300 ml culture volume was used, and the supernatant was collected.

(g) Preparation and cultivation of peritoneal macrophages

Two milliliter of 4% thioglycolate (Difco) was intraperitoneally administered to ICR mice (Japan SLC), and the mice were killed by chloroform anesthesia 3 days later. The abdominal cavities were washed two times with 5 ml of Hanks' solution (Nissui Pharmaceutical) containing 5 U/ml of heparin (Wako Pure Chemical). The resulting cells were washed with RPMI1640, and suspended in 100 $\mu$l of 10% FCS-RPMI1640, and $1 \times 10^6$ of those cells were inoculated to a flat-bottom plate (24-well), and cultured.

(h) Purification of antibody

The antibodies were purified by using HiTrap Protein G (Pharmacia). The column was washed with a starting buffer (20 mM sodium biphosphate, pH 7.0) in an amount of more than three times of the column volume, and equilibrated with 2 ml of the starting buffer. Then, the culture supernatant of the above hybridomas was applied to the column by using a peristaltic pump (ATTO). The column was washed with 5 ml of the starting buffer, and the antibodies were eluted with 3–5 ml of an elution buffer (0.1 M glycine/HCl, pH 2.7) into a tube containing 100 $\mu$l of 1 M Tris-HCl. The eluted fractions were dialyzed against phosphate buffered saline (PBS), assayed for the antibody concentration by a protein assay according to the BCA method (Bicinchoninic acid method, Smith P. K. et al., Analytical Biochem., 150, 76–85, 1985), and sterilized by filtration through a filter (0.45 $\mu$m) to afford an antibody sample. The sample was stored at 4° C. These antibodies were designated 4C1 antibodies.

Example 2

Subclass determination

Dilutions of the following antibodies, all of which were from SIGMA, were prepared with 0.1 M hydrogencarbonate buffer (pH 9.6): anti-rat IgG1 antibodies (500-fold dilution), anti-rat IgG2a antibodies (5000-fold dilution), anti-rat IgG2b antibodies (1000-fold dilution), and anti-rat IgG2c antibodies (500-fold dilution). 50 $\mu$ of each was introduced into to each of 2 wells of a 96-well plate (NCNC), and incubated at 4° C. overnight. The wells were washed with PBS containing 0.05% Tween-20 (PBST), blocked with PBST containing 0.5% bovine serum albumin (BPBST) at 37° C. for 40 minutes, added with 50 $\mu$l of the antibody sample mentioned above (4C1 antibodies), and allowed to react at 37° C. for 40 minutes. Then, the plate was washed with PBST, added with 50 $\mu$l of peroxidase-labeled goat anti-rat IgG (10000-fold dilution, GIBCO BRL), and allowed to react at 37° C. for 40 minutes. Thereafter, appropriate color development was obtained with a peroxidase substrate (TMB micro peroxidase substrate system, KPL), the reaction was stopped with 1N phosphate, and absorbance at 450 nm (control: 630 nm) was measured by a microplate reader. As a result, it was found that the 4C1 antibodies were IgG2b subclass antibodies. Accordingly, anti-rat IgG2b monoclonal antibodies that do not recognize CD14 and do not have reactivity for macrophages (4B12 antibodies) were used as control antibodies in the following examples.

Example 3

Molecular weight determination of antigen recognized by 4C1 antibody $1 \times 10^8$ of RAW 264.7 cells were suspended in 1 ml of PBS, reacted with 100 $\mu$l of NHS-biotin (Bio-Rad) for 30 minutes on ice, washed with PBS, and then treated in solubilization buffer (stock solution containing 20 mM Tris-HCl, 140 mM NaCl, 2 mM EDTA, pH 8.2, 1% NP-40 [Calbiochem-Navabiochem], 5 mM iodoacetamide, (SIGMA), 1 mM phenylmethanesulfonyl fluoride (PMSF, SIGMA), and 50 $\mu$M 4-(2-aminoethyl)benzenesulfonyl fluoride (AEBSF, SIGMA)) for 30 minutes on ice to solubilize the cells. Then, the mixture was centrifuged (15000 rpm, 10 minutes), and the resulting supernatant was used as an immunoprecipitation sample.

This supernatant (100 $\mu$l) and 50 $\mu$l of agarose anti-rat IgG (Cappel) were shaken together at 4° C. overnight, and centrifuged. The supernatant was allowed to react with the monoclonal antibodies of the present invention or control monoclonal antibodies (5 $\mu$g each) by shaking together at 4° C. for 2 hours, and allowed to react with 10 $\mu$l of agarose anti-rat IgG by shaking together at 4° C. for 1 hour. The mixture was centrifuged at 3000 rpm for 5 minutes, and the supernatant was removed. The precipitates were washed with the solubilization buffer 5 times, added with 40 $\mu$l of sample buffer, and heated to 100° C. for 5 minutes. The resulting mixture (30 $\mu$l) was applied to 10% polyacrylamide gel to perform sodium dodecylsulfate polyacrylamide gel electrophoresis (SDS-PAGE). The products were transferred to a polyvinylidene fluoride (PVDF) membrane (Japan Genetics) at 200 mA for 1.5 hours. The membrane after the transfer was washed with PBST for 15 minutes, and blocked by shaking with 3% BSA-PBS at 4° C. overnight or at 37° C. for one hour. Then, the membrane was added with streptavidin peroxidase (2500-fold dilution), shaken at 37° C. for one hour, and washed with PBST, and chemiluminescence was obtained from the bands with ECL Western Blotting Detection System (Amersham), and exposed to an X-ray film (X-OMAT, Kodak).

The molecular weight of the resulting band was determined by simultaneously electrophoresing samples and biotin-labeled SDS-PAGE standards (BIO-RAD) as the molecular weight markers. The results are shown in FIG. 1.

Figure 1:
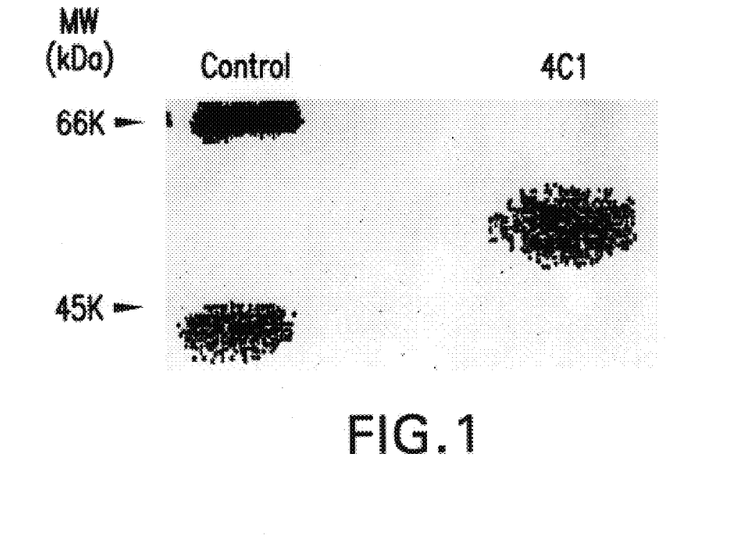
FIG. 1 shows the result of SDS-PAGE of the antigen which binds to the 4C1 antibodies and was obtained from immunoprecipitation of biotin-labeled RAW 264.7 cell lysate.

As shown in FIG. 1, the band of the antigen which had been recognized by the 4C1 antibodies of the present invention was observed at a molecular weight of around 52–57 kDa.

Example 4
Determination of molecular structure of antigen recognized by 4C1 antibody Each of RAW 264.7 cells, bone marrow macrophages, and casein-induced granulocytes were suspended in 2% FCS-PBS, and allowed to react with 0.125 U/ml of phosphatidylinositol specific phospholipase C (PI-PLC, Funakoshi) at 37° C. for 30 minutes. Then, the cells were washed, and allowed to react with 2 μg of the 4C1 antibodies for 30 minutes on ice. Thereafter, the cells were washed twice with 2% FCS-PBS, resuspended in 50 μl of 2% FCS-PBS, and allowed to react with 0.4 mg/ml of fluorescein isothiocyanate (FITC) goat anti-rat IgG of (H+L), F(ab')$_2$ (Wako Pure Chemical) for 30 minutes on ice. After the reaction, the cells were washed twice with 2% FCS-PBS, suspended in 400 μl of 2% FCS-PBS, and added with 100 μl of 10% neutral buffered formaldehyde solution (Nakarai Tesque) to fix the cells, which were analyzed by a fluorescence-activated cell sorter (FACS). The control antibodies (4B12 antibodies) were treated in the same manner as above, and similarly analyzed by FACS. The results of the FACS analysis are shown in Table 1. As seen from the results shown in Table 1, the fluorescence intensity of the PI-PLC treated cells was reduced compared with untreated cells, indicating that the antigen of the 4C1 antibodies was glycosylphosphatidylinositol-binding type (GPI anchor type) protein that is degraded by PI-PLC.

TABLE 1

| | PI-PLC treatment Average fluorescence intensity | | | |
|---|---|---|---|---|
| | Control antibody | | 4C1 antibody | |
| Cell | (−) | (+) | (−) | (+) |
| RAW264.7 | 5.8 | 6.9 | 49.8 | 8.5 |
| Bone marrow macrophage | 7.6 | 6.7 | 31.9 | 7.2 |
| Granulocyte | 9.2 | 7.1 | 77.7 | 45.6 |

Example 5
Western blot analysis utilizing anti-CD14 antibody

1×10$^8$ of RAW 264.7 cells were solubilized by a treatment in the solubilization buffer for 30 minutes on ice, and centrifuged (15000 rpm, ten minutes), and the resulting supernatant was used as an immunoprecipitation sample.

This supernatant (100 μl) and 50 μl of agarose anti-rat IgG antibodies (Cappel) were allowed to react by shaking together at 4° C. overnight, and centrifuged. The supernatant was allowed to react with 5 μg each of known CD14 antibodies (rmC5-3, Pharmingen), the 4C1 antibodies, or control antibodies (4B12 antibodies) by shaking together at 4° C. for two hours, and further allowed to react with 10 μl of agarose anti-rat IgG antibodies (Cappel) by shaking together at 4° C. for one hour. This reaction mixture was centrifuged at 3000 rpm for five minutes, and the supernatant was removed. The precipitates were washed 5 times with the solubilization buffer, added with 40 μl of the sample buffer, and heated to 100° C. for 5 minutes. The resultant mixture (30 μl) was applied to 10% polyacrylamide gel to perform SDS-PAGE.

Then, the electrophoresed proteins were transferred to a PVDF membrane (Japan Genetics) at 200 mA for 1.5 hours. The membrane after the transfer was washed with PBS for 15 minutes, and blocked by shaking with 3% BSA-PBS at room temperature for 2 hours. Then, the membrane was reacted with known anti-CD14 antibodies (rmC5-3) at 4° C. overnight. After the reaction, the PVDF membrane was shaken with peroxidase-labeled goat anti-rat IgG antibodies (5000-fold dilution, GIBCO BRL) at room temperature for 2 hours, and washed with PBS. Then, chemiluminescence was obtained from the bands with ECL Western Blotting Detection System (Amersham), and exposed to an X-ray film (X-OMAT, Kodak). The molecular weight of the resulting band was determined by using Kaleioscope prestained standards (BIO-RAD) as the molecular weight markers. The results are shown in FIG. 2.

Figure 2:
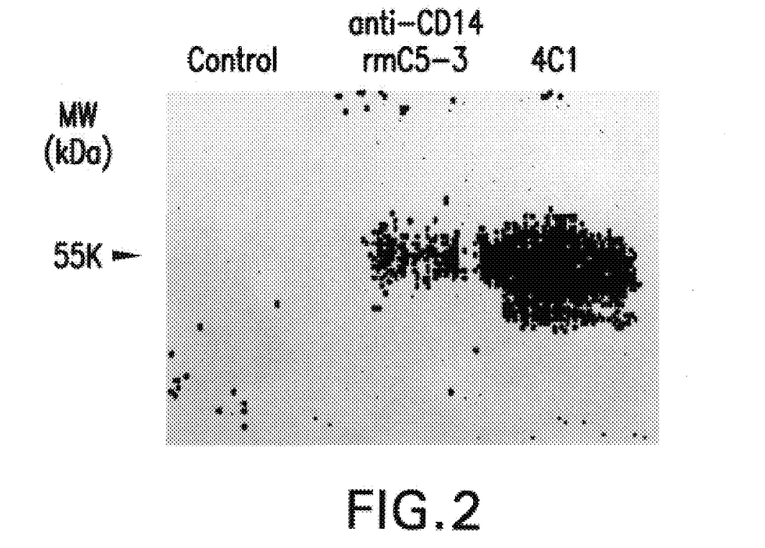
FIG. 2 shows the result of SDS-PAGE of the antigen which binds to the 4C1 antibodies and was obtained from immunoprecipitation of RAW 264.7 cell lysate with the 4C1 antibodies.

As shown in FIG. 2, a band was found in the product of the immunoprecipitation by the 4C1 antibodies, whose molecular weight corresponded to that of a product found in the immunoprecipitation products obtained with the known CD14 antibodies (rmC5-3). On the other hand, such a band was not detected in the immunoprecipitation products obtained with the control antibodies (4B12 antibodies). The results of Examples 3 and 4 and this example demonstrate that the 4C1 antibodies were antibodies recognizing mouse CD14.

Example 6
Binding of 4C1 antibody to cell pretreated with anti-mouse CD14 antibody (rmC5-3)

Binding of the 4C1 antibodies to cells pretreated with CD14 antibodies (mrC5-3) was analyzed by FACS using a complex composed of the 4C1 antibody labeled with FITC (FITC-binding 4C1 antibody).

(a) Labeling of 4C1 antibody with FITC

The 4C1 antibodies were dialyzed against a buffer for labeling with fluorescein isothiocyanate (FITC) (0.05 M boric acid, 0.2 M NaCl, pH 9.2) at 4° C. for two days. After the dialysis, absorbance $A_{280}$ was measured to determine the antibody concentration (antibody concentration [mg/ml]= $A_{280}$×0.74 ×times of dilution). 20 μl of 5 mg/ml FITC solution in dimethyl sulfoxide was added to 1 mg of the 4C1 antibodies, and allowed to react at room temperature for two hours. Then, the reaction mixture was dialyzed against a dialysis buffer (0.1 M Tris-HCl, 0.1% (v/v) NaN$_3$, 0.2 M NaCl, pH 7.4) at 4° C. for two days. After the dialysis, absorbances $A_{280}$ and $A_{492}$ of the dialyzed internal solution were measured to determine the concentration of the FITC-binding 4C1 antibodies (protein (mg/ml)=$A_{280}$−($A_{492}$× 0.35)/1.4).

(b) Binding of 4C1 antibody to cells treated with anti-mouse CD14 antibody (mrC5-3)

RAW 264.7 cells (1×10$^6$ cells) were suspended in 50 μl of 2% FCS-PBS, and reacted with 5 μl each of the 4C1 antibodies, known CD14 antibodies (mrC5-3), or the control antibodies for 30 minutes on ice. Then, the cells were washed twice with 2% FCS-PBS, resuspended in 50 μl of 2% FCS-PBS, and reacted with 0.5 μg of FITC-binding 4C1 antibodies for 30 minutes on ice. After the reaction, the cells were washed twice with 2% FCS-PBS, suspended in 50 μl of 2% FCS-PBS, and added with 100 μl of 10% neutral buffered formaldehyde solution (Nakarai Tesque) to fix the cells. Thereafter, the concentration of FITC-binding 4C1 antibodies binding to the cells was determined in the same manner as described above. Untreated RAW 264.7 cells were also reacted with FITC-binding 4C1 antibodies, and the concentration of the binding antibodies was determined. The results are shown in FIG. 3.

Figure 3:
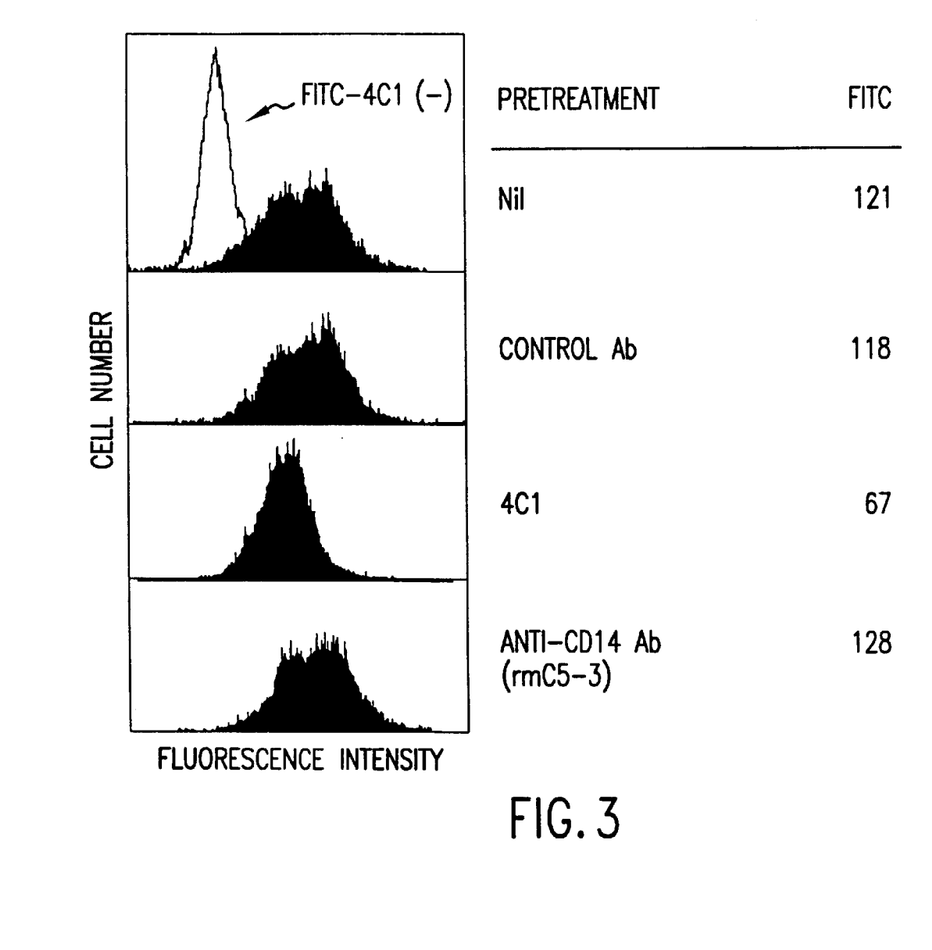
FIG. 3 shows the result of FACS analysis of binding property of the 4C1 antibodies to RAW 264.7 cells treated with CD14 antibodies.

As shown in FIG. 3, fluorescence intensity of the cells pretreated with the unlabeled 4C1 antibodies was reduced, indicating that the binding of the FITC-binding 4C1 antibodies to the cells was inhibited. However, fluorescence intensity of the cells pretreated with the known CD14 antibodies (rmC3-5) was not reduced. The results demonstrate that the 4C1 antibodies were bound to an epitope different from that recognized by the known CD14 antibodies (rmC3-5).

Example 7

Effect of 4C1 antibody on cytokine production induced by LPS

Figure 4A:
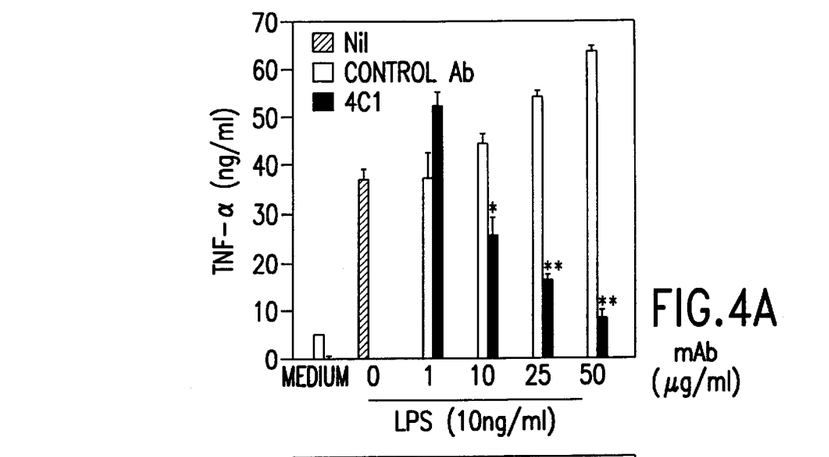
FIGS. 4A–C shows the results of the test for inhibitory effect of the 4C1 antibodies on the cytokine and NO production by RAW 264.7 cells stimulated with LPS.
Figure 4B:
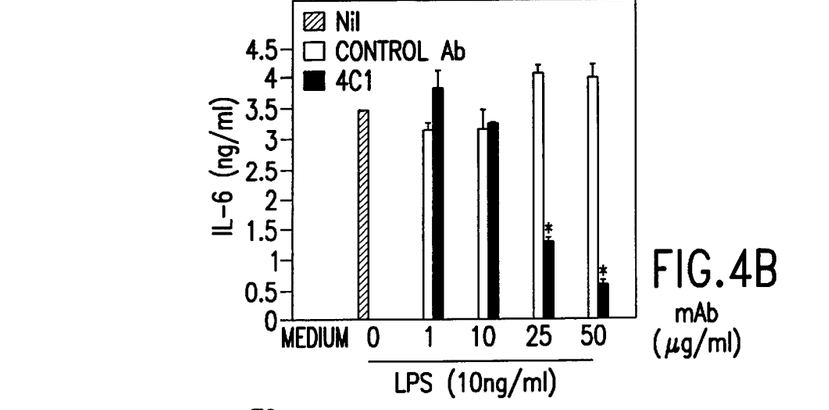
Figure 4C:
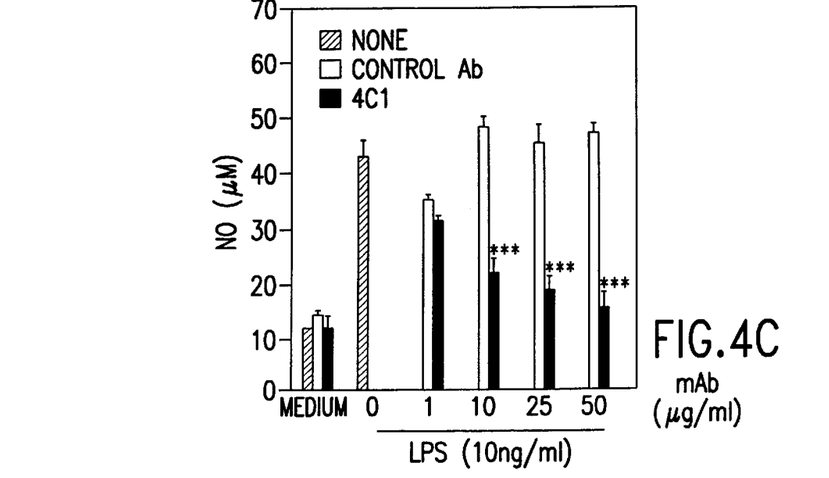

RAW 264.7 cells were inoculated to each well of a 24-well plate at a concentration of $1 \times 10^6$ cells/ml, and cultivated in the presence of LPS (10 ng/ml) and the 4C1 antibodies at various concentrations indicated in FIG. 4 (1, 10, 25, and 50 µg/ml), and the amounts of TNF-α and IL-6 in the resulting culture supernatant were measured by ELISA, and the amount of NO (nitrous acid) by using Griess reagent. The cultivation time was 12 hours for the measurement of TNF-α and NO, and 24 hours for IL-6. The results are shown in FIGS. 4 (a)–(c).

As shown in FIGS. 4 (a)–(c), the 4C1 antibodies concentration-dependently suppressed the production of TNF-α, IL-6 and NO induced by LPS in macrophages. These results show that the 4C1 antibodies suppressively act on the functions of macrophages.

Example 8

Figure 5A:
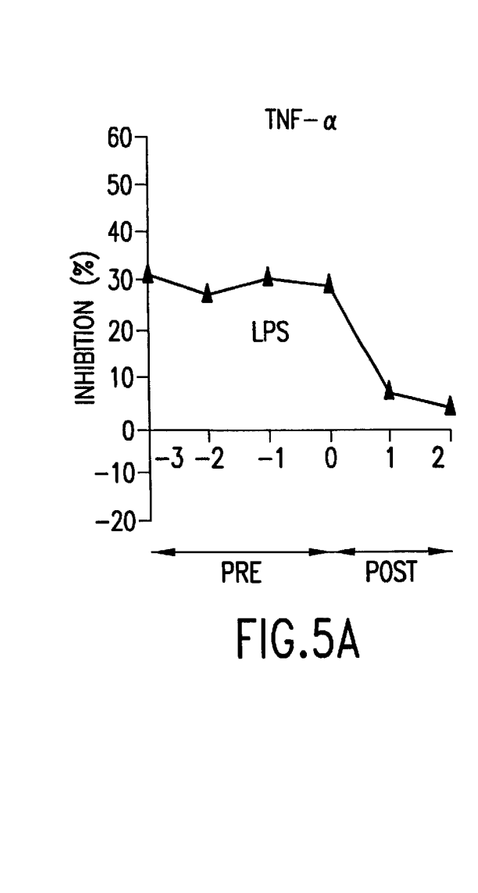
FIG. 5 shows the results of the test for inhibitory effect of the 4C1 antibodies on activation of RAW 264.7 cells.
Figure 5B:
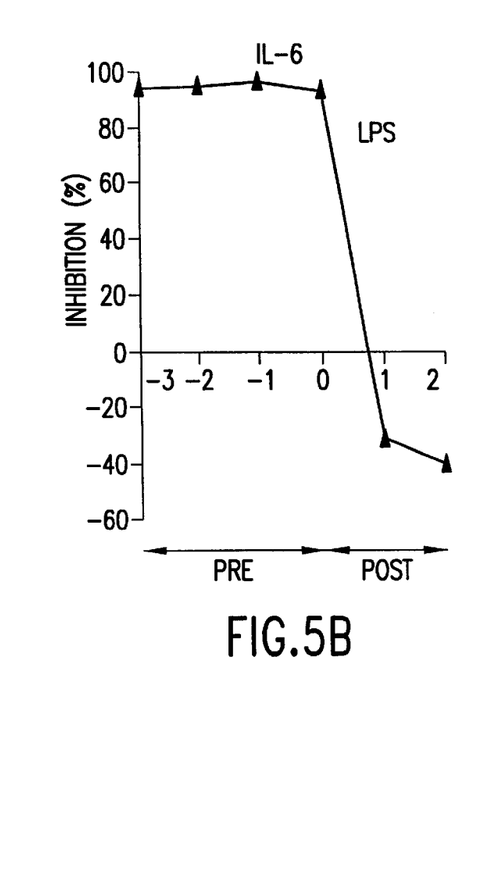
Figure 5C:
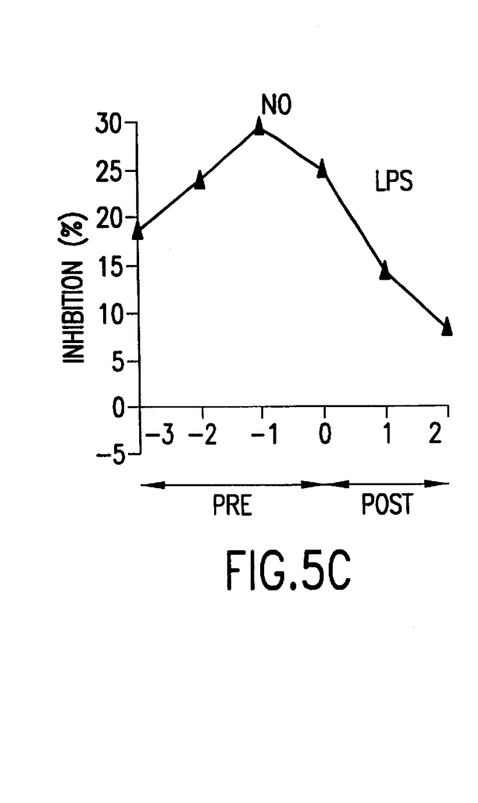

Functional variation of macrophage by treatment with 4C1 antibody at various time points RAW 264.7 cells were cultured in the same manner as in Example 7, but the RAW 264.7 cells were treated with the 4C1 antibodies (100 µl) at the points of 3, 2 and 1 hours before, and 0, 1 and 2 hours after the stimulation by the addition of LPS, and cultured for 12 hours for the measurement of TNF-α and NO, and 24 hours for IL-6. The amounts of TNF-α, IL-6 and NO induced by LPS were determined in the same manner as in Example 7. The results are shown in FIG. 5. The results are represented by reduction ratio of cytokine production (production suppression ratio) relative to the case where the 4C1 antibodies were not added.

As shown in FIG. 5, when the cells were treated before the stimulation with the 4C1 antibodies or simultaneously (0 hour), the production of TNF-α, IL-6 and NO induced by LPS was suppressed. As for the production of IL-6, high suppression ratio was observed from the treatment 3 hours before the stimulation to the simultaneous treatment, whereas no suppression was observed at all when the cells were treated after the stimulation. As for the production of TNF-α and NO, when the cells were pretreated, the suppression ratio was relatively low compared with that of IL-6, i.e., 30–50% for TNF-α, and 15–30% for NO, and when they were treated after the stimulation, as with IL-6, substantially no suppression was observed. These results demonstrate that the 4C1 antibodies suppressively act on earlier stages of the activation of macrophages.

Example 9

Analysis of LPS binding inhibition utilizing FITC-binding LPS

RAW 264.7 cells ($1 \times 10^6$) were suspended in 100 µl of 10% FCS-RPMI1640, added with LPS (500 µg/ml), 4C1 antibodies (25 µg/ml), or 4B12 antibodies as control, in the presence of FITC-binding LPS (5 µg/ml, SIGMA), and allowed to react at 4° C. for 18 hours. Then, the cells were suspended in 50% FCS-PBS, and centrifuged. After removing the supernatant, the cells were suspended in 2% FCS-PBS, and analyzed by FACS. The results are shown in FIG. 6.

Figure 6:
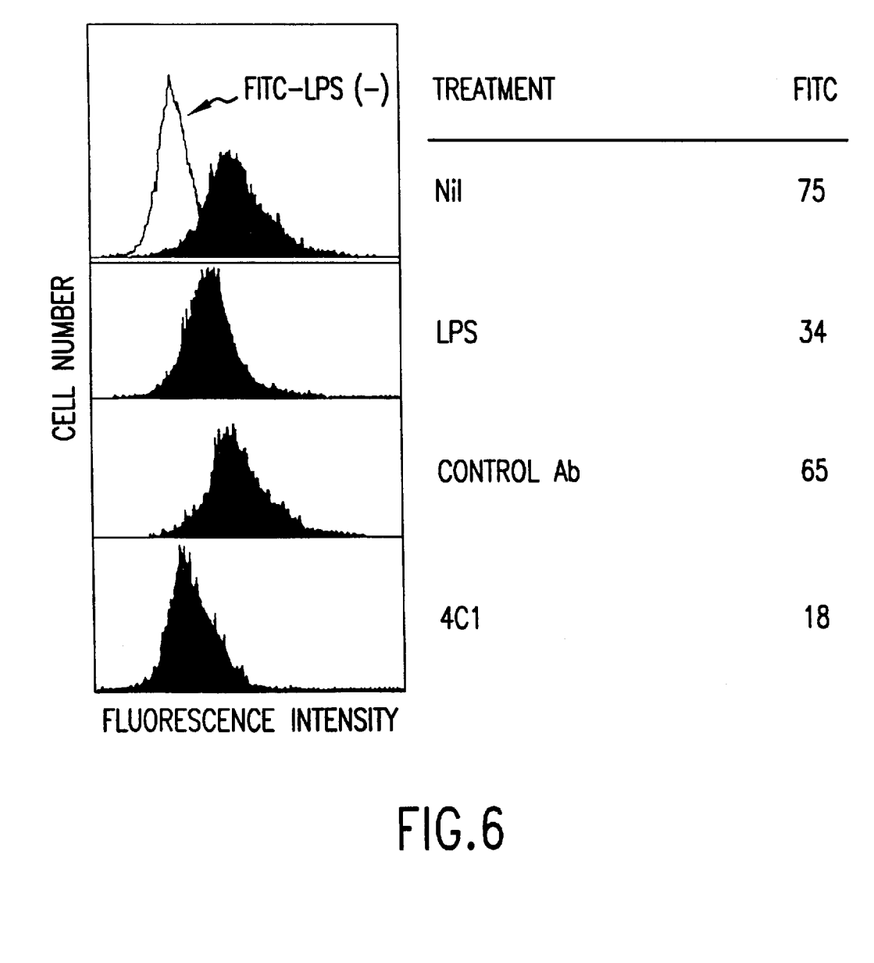
FIG. 6 shows the results of the test for competitive effect of the 4C1 antibodies on FITC-labeled LPS binding to RAW 264.7 cells.

As shown in FIG. 6, when unlabeled LPS coexisted in 100 times amount of FITC-binding LPS, fluorescence intensity was reduced compared with that obtained with the cells cultured in the absence of the reagent (no treatment), and therefore it was demonstrated that the binding of FITC-binding LPS to macrophages was inhibited. Further, it was also demonstrated that the binding of FITC-binding LPS to macrophages was similarly inhibited when the 4C1 antibodies coexisted. On the other hand, when the control antibodies (4B12 antibodies) were used, such a phenomenon was not observed. These results demonstrate that the recognition site of the 4C1 antibodies is the LSP-binding site of CD14, and that the suppressive action of the 4C1 antibodies on the cytokine and NO production induced by LPS is caused by the inhibition of binding of LPS to the binding site on cell surface by the 4C1 antibodies.

The monoclonal antibody of the present invention suppresses the production of an inflammatory mediator such as TNF, IL-6 and NO at early stages by recognizing the lipopolysaccharide binding site of the cell surface receptor CD14, and competitively inhibiting its binding with LPS. Therefore, it is useful for analysis of the critical mechanism of sepsis, and the treatment thereof.

What is claimed is:

1. A monoclonal antibody which is produced by the hybridoma FERMBP-6924.

* * * * *